United States Patent
Peecock

(10) Patent No.: US 7,497,617 B2
(45) Date of Patent: Mar. 3, 2009

(54) X-RAY MANIPULATOR

(75) Inventor: Benjamin Kingsley Stuart Peecock, Suffolk (GB)

(73) Assignee: Nordson Corporation, Westlake, OH (US)

( * ) Notice: Subject to any disclaimer, the term of this patent is extended or adjusted under 35 U.S.C. 154(b) by 0 days.

(21) Appl. No.: 11/571,541

(22) PCT Filed: Jul. 4, 2005

(86) PCT No.: PCT/GB2005/002611

§ 371 (c)(1),
(2), (4) Date: Dec. 7, 2007

(87) PCT Pub. No.: WO2006/003430

PCT Pub. Date: Jan. 12, 2006

(65) Prior Publication Data

US 2008/0232551 A1 Sep. 25, 2008

(30) Foreign Application Priority Data

Jul. 5, 2004 (GB) ................................. 0415053.8

(51) Int. Cl.
*H05G 1/02* (2006.01)
*H05G 1/00* (2006.01)

(52) U.S. Cl. ........................................ 378/195; 378/208

(58) Field of Classification Search ................... 378/20, 378/57, 70, 81, 90, 177, 195, 207, 208
See application file for complete search history.

(56) References Cited

U.S. PATENT DOCUMENTS

| 3,728,541 | A | 4/1973 | Rabinovich et al. | |
| 6,005,914 | A | 12/1999 | Quinn et al. | |
| 6,859,520 | B2 * | 2/2005 | He et al. | 378/79 |
| 6,882,739 | B2 * | 4/2005 | Kurtz et al. | 382/109 |
| 2003/0058984 | A1 | 3/2003 | Susami et al. | |

FOREIGN PATENT DOCUMENTS

EP 1376108 A2 1/2004

* cited by examiner

*Primary Examiner*—Irakli Kiknadze
(74) *Attorney, Agent, or Firm*—Wood, Herronn & Evans, L.L.P.

(57) ABSTRACT

A frame (10) for an x-ray inspection device comprises a structural member (16) to which is pivoted an arcuate frame (21). An x-ray source (12) is in use mounted directly to the member (16), and an x-ray detector (13) is movable around the frame (21). A three axis sample support for items to be imaged is arranged between the source (12) and detector (13). The frame (10) of the invention is particularly rigid.

10 Claims, 3 Drawing Sheets

X-RAY MANIPULATOR

The present invention relates to an x-ray manipulator, and particularly to a manipulator adapted for viewing the internal structure of miniature electrical devices.

X-rays are produced when a suitable target is energized by an electron beam. As is well known certain materials absorb x-rays better than others and accordingly the internal structure of a component can be imaged from a suitable x-ray detector. In particular a high degree of magnification is possible by increasing the distance from the x-ray source to the detector with respect to the distance from the source to the object being imaged.

When imaging at high magnification, it is important to reduce the x-ray source to the smallest possible spot. Only by this means can the edge definition of the image be sharp. However, when the spot is very small, movement within the x-ray device can seriously affect the prospects of obtaining good edge definition at high magnification. Such movement may for example be as a result of external vibration, or as a result of relative movement between the components of the device.

The problems of movement between components of an x-ray inspection device are also influenced by the requirement for relative movement between those parts. For example, the detector may be permitted relative angular movement in several planes in order to provide an image of the object from several directions. The object may also be movable on three axes, both to change the magnification, and to maintain the object within the field of view of the detector.

What is required is an x-ray inspection device which substantially overcomes the aforementioned problems.

According to the invention there is provided a frame for an x-ray inspection device and comprising a structural member having a sample support mounted thereon for movement in three mutually perpendicular planes; the structural member being adapted for direct mounting of an x-ray generator on one side of said sample support, and having an arcuate frame pivotable thereon on the other side of said sample support; the arcuate frame having an arcuate track thereon and the track being adapted to mount an x-ray detector for movement around the arcuate frame.

Mounting the x-ray generator directly to the structural member eliminates so far as possible any vibration or movement with respect thereto, and accordingly the edge definition of an image is improved. It will be understood that if any flexibility of the mounting is permitted, the effective diameter of the x-ray spot may be somewhat larger than the true diameter, and this results in x-rays being stimulated over a larger area than intended, and increased fuzziness around the edges of an image.

The structural member of the frame has all elements of the inspection device directly mounted thereon and can thus eliminate internal vibration and movement to the greatest possible extent.

The use of an adequately stiff structural member ensures precise relative positioning of the three main elements which are mounted thereto, namely the x-ray generator, the sample support manipulator (pan & zoom) and the x-ray detector. Furthermore, the use of a single mounting for these three components minimises the build-up of tolerance which is inherent in any assembly of parts. Accordingly the invention results in a device which can be assembled easily, with the main components fixed in any order, and with the assurance of accuracy and precision.

Maintenance of the device is also substantially improved because the structural member is essentially internal, and as a consequence is small and light when compared with constructions relying in whole or in part on an external frame. Such external frames are inevitably heavy and have poor dimensional tolerances and stiffness. Because the structural member is internal, the device permits all-round accessibility to the components mounted thereon. Additionally, direct separate mounting of the components ensures that they can be removed for maintenance or replacement with the assurance that re-fitting is accurate, and the relative alignment of other main components is not disturbed.

By arranging the structural member low down, the stability of the device is further increased.

Necessarily relative movement of the arcuate member and sample support is required, for which suitable high precision slideways and bearings can be employed. The structural member is preferably of metal, and in the preferred embodiment is of aluminium.

In the preferred embodiment the structural member substantially comprises a plate having the arcuate member pivoted about opposite ends thereof, the sample support mounted to one side thereof, and adapted to receive the x-ray generator on the other side thereof. Preferably the plate is arranged in a vertical plane with the x-ray generator below, and the x-ray detector above. In this way the sample support is generally horizontal, and the x-rays impinge on the sample from below. Furthermore the plate provides a suitable direct mounting for the Z axis slideways of the sample support.

In the preferred embodiment the plate is substantially rectangular and extends at full depth between bearings of the arcuate frame. Preferably the plate is below the pivoting axis of the arcuate frame, and in the preferred embodiment is offset to one side of said axis to permit the axis of the electron beam of the x-ray generator to pass through the pivoting axis of the frame.

In the preferred embodiment, the plate includes a perimeter frame in a plane at right angles thereto and on the axis of said arcuate frame, the perimeter frame providing spaced mounting points for location of the device in an x-ray cabinet.

This arrangement allows the perimeter frame to support the device on generally upright mountings, the support plate being arranged in the space between these mountings.

In the preferred embodiment the arcuate frame includes counterweights below the pivoting axis so as to tend to return the frame to an upright condition. Preferably the x-ray detector is substantially on one side of the frame, and on the other side of the frame is provided a motor for driving the detector around said track. Such an arrangement allows the detector/motor assembly to be balanced on the frame.

The perimeter frame may comprise slideways mountable on rails, the rails being for support by mountings within the cabinet. This arrangement allows the inspection device to be moved transversely with respect to the mountings, and typically out of an x-ray cabinet, for maintenance and repair. Suitable means for locking the device on the rails are provided.

In the preferred embodiment the upright mountings for the device comprise self levelling air bearings.

Other features of the invention will be apparent from the following description of a preferred embodiment illustrated by way of example only in the accompanying drawings in which.

Figure 1:
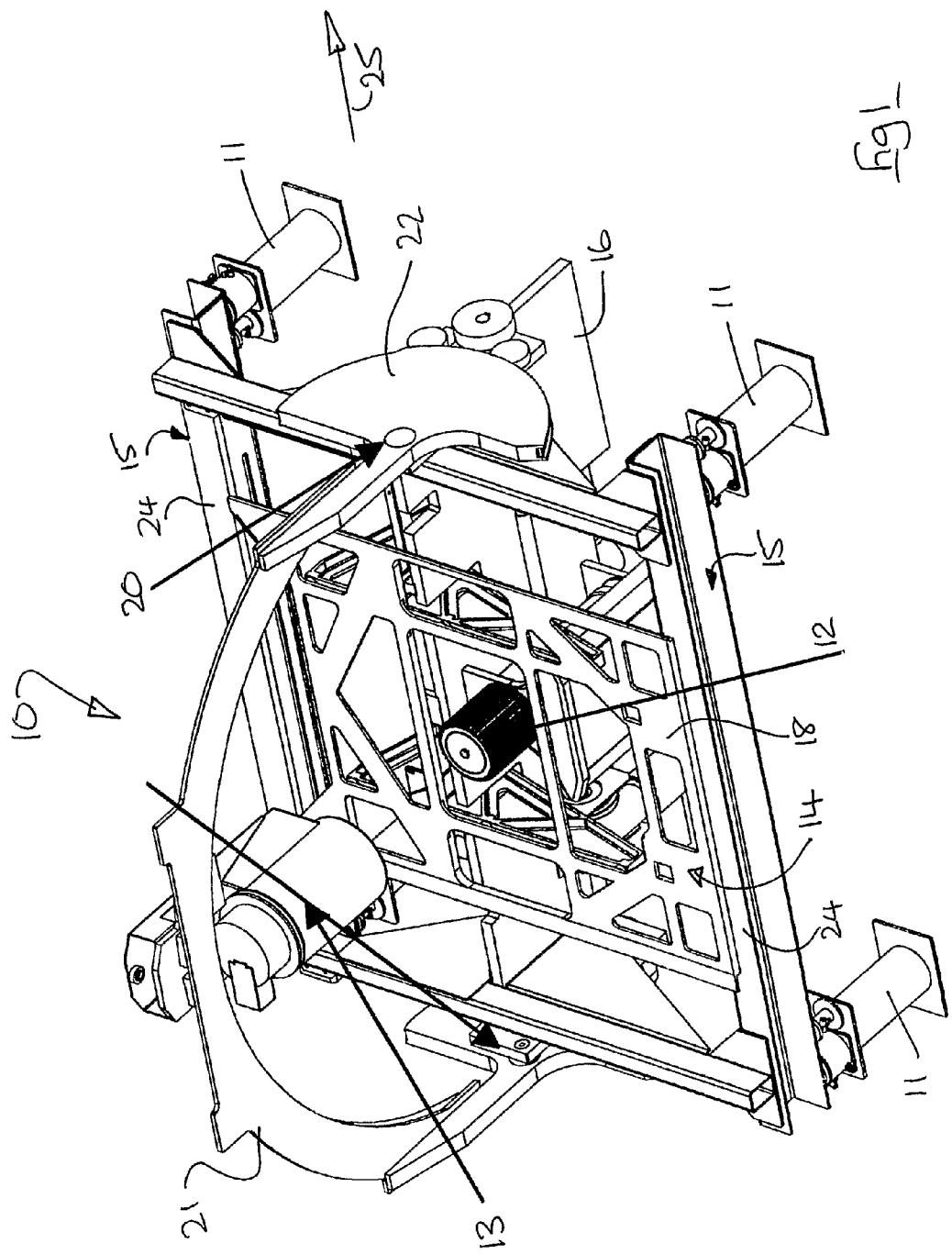
FIG. 1 illustrates a device according to the invention from above and one side.
Figure 2:
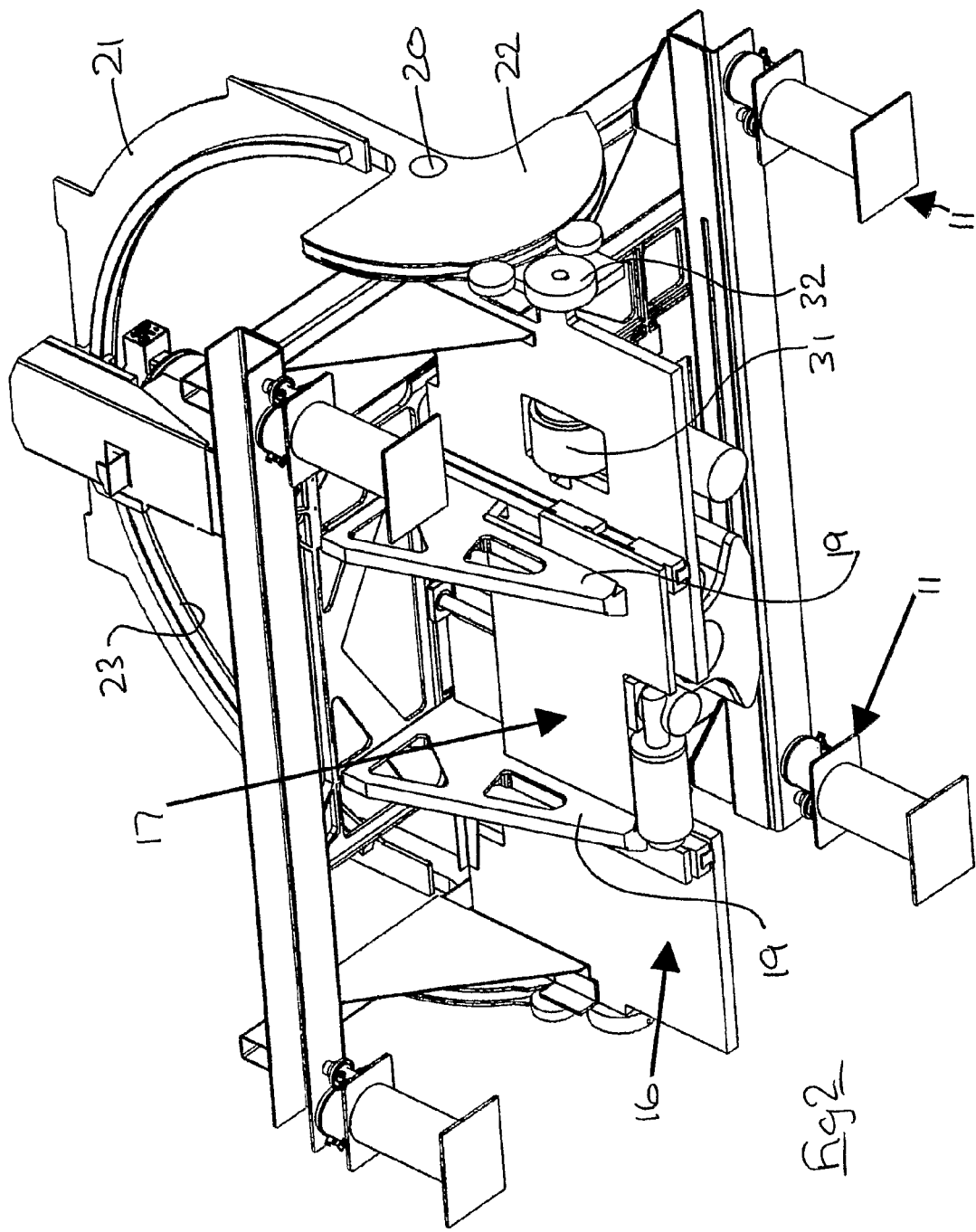
FIG. 2 illustrates a device according to the invention from below and the opposite side.

With reference to the drawings, a frame 10 is supported on feet 11 which themselves are mounted within a cabinet (not shown). This cabinet is of the usual kind and provides a shielded enclosure to protect users from the harmful effects of x-rays. Mounted on the frame is an x-ray tube 12 for generating x-rays, and an x-ray detector 13. Between the tube 12 and detector 13 is movable plate 14 adapted to support an object to be imaged.

Each foot 11 comprises an anti-vibration mount comprising a self levelling air bearing of a known kind. Air under pressure is supplied to the bearing, and substantially isolates the frame from externally applied vibrations which may be transmitted to the cabinet.

The air bearings are in pairs and arranged at the corners of a rectangle. Each pair of bearings 11 supports a respective beam 15 on which the frame 10 is mounted.

The frame 10 comprises a main support plate 16 arranged between the beams 15 in a substantially vertical plane. The support plate 16 is relatively massive and rigid and comprises the principal structural element of the frame 10.

To one side of the support plate 16 is directly mounted the x-ray tube 12. The tube 12 is generally central with respect to the feet 11, and thus it will be appreciated that the plate is slightly offset to one side.

On the other side of the support plate 16 is directly mounted one leg 17 of the movable plate 14 on which a sample is placed in use. This leg 17 is slidable vertically (in the Z axis) with respect to the support plate on suitable slideways and under the control of an electric motor.

The other leg of the movable plate 14 comprises an X-Y table constituted by the open framework 18. Rigidity between the leg 17 and framework 18 is assured by means of relatively massive brackets 19, as illustrated. X-Y movement of the table is provided by suitable slideways and under the control of electric motors.

The lateral ends of the support plate 16 have rigid cheeks on which are directly mounted bearings 20 of an arcuate frame 21. The ends of the frame comprise counterweights 22. The inner side of the frame comprises a track 23 which follows the circumference of a circle centred on the x-ray source of the tube 12.

Mounted on the track 23 is the x-ray detector (or image intensifier) 13. Suitable electric motors allow movement of the intensifier 13 along the track 23, and arcuate movement of the arcuate frame 21 about the support plate 16. It will be understood that the detector 13 can be moved around the x-ray source from the vertical, generally in the range±60°.

A generally rectangular perimeter frame 24 provides support for the X-Y table, and is also directly anchored to the support plate 16. The side members of the frame 24 may be constituted by the beams 15, or by separate members mountable on the beams, as will be further described below. In use a sample tray is provided, generally in the central aperture of the framework 18, and a sample to be imaged is placed on the tray. The cabinet is closed, and the x-ray tube energized to stimulate the production of x-rays. These x-rays radiate in straight lines from the spot source, and the detector 13 and/or framework 18 is moved until the sample is imaged in the desired orientation. The image may for example be displayed on an external screen of the cabinet provided adjacent to suitable manipulator controls, such as one or more joysticks. The relative position to the sample and/or detector may be moved in real time to image the sample from the desired direction and at the appropriate magnification.

The perimeter frame 24 can be mounted on separate beams 15 by wheels (not shown) to permit lateral relative movement of the frame in the direction of arrow 25. This arrangement allows the inspection device to be pulled at least partially out of an x-ray cabinet for inspection and repair. Typically a lateral movement corresponding to 50-60% of the depth of the device can be accommodated.

Figure 3:
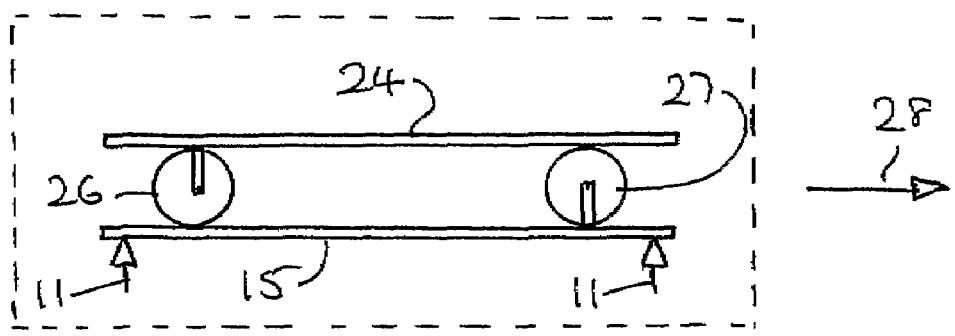
FIG. 3 is a schematic side view of a rolling mounting for the device.

This arrangement is illustrated schematically in FIG. 3 whereby the frame 24 has a pair of support wheels 26, and support beams 15 have a pair of support wheels 27. Rolling movement in the direction of arrow 28 permits the frame to be moved laterally with respect to a cabinet represented by dotted line 29. The feet 11 for the frame are represented by arrows.

Figure 4:
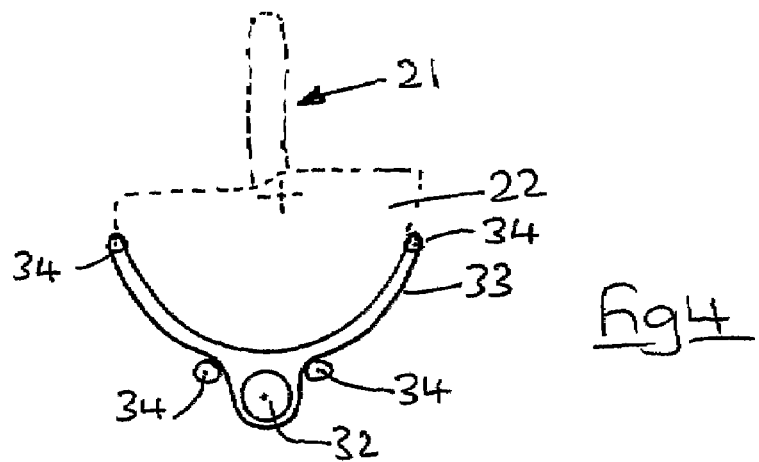
FIG. 4 is a schematic view of a belt drive arrangement.

The drive arrangement for the arcuate frame 21, is illustrated in FIG. 4 and comprises a motor 31 mounted below the counterweight on the support plate 16, and having a pulley 32 driving an endless toothed belt 33.

The belt is guided by jockey wheels 34 and is movable in either direction to pivot the frame 21 about its axis. A toothed belt provides accurate substantially lash free drive in either direction without the need for lubrication.

A similar toothed belt drive arrangement is provided for the detector 13 whereby a motor 36 mounted on the arcuate frame 21 drives an endless toothed belt which follows the path of the track 23. By this means the detector can be driven smoothly in either direction.

The invention claimed is:

1. A frame for an x-ray inspection device and comprising a structural member having a sample support mounted thereon for movement in three mutually perpendicular planes; the structural member being adapted for direct mounting of an x-ray generator on one side of said sample support, and having an arcuate frame pivotable thereon on the other side of said sample support; the arcuate frame having an arcuate track thereon and the track being adapted to mount an x-ray detector for movement around the arcuate frame.

2. A frame according to claim 1 wherein the structural member substantially comprises a plate having the arcuate member pivoted about opposite ends thereof, the sample support mounted to one side thereof, and adapted to receive the x-ray generator on the other side thereof.

3. A frame according to claim 2 wherein the plate is arranged in a vertical plane in use, and adapted for the x-ray generator below, and the x-ray detector above.

4. A frame according to claim 3 wherein said plate provides a direct mounting for Z axis slideways of the sample support.

5. A frame according to claim 2 wherein said plate is substantially rectangular and extends at full depth between bearings of the arcuate frame.

6. A frame according to claim 5 wherein said plate is below the pivoting axis of the arcuate frame.

7. A frame according to claim 6 wherein said plate is offset to one side of said axis to permit an electron beam of an x-ray generator to pass through said axis.

8. A frame according to claim 2 wherein said plate includes a perimeter frame in a plane at right angles thereto and on the axis of said arcuate frame, the perimeter frame being adapted to provide spaced mounting points for location in an x-ray cabinet.

9. A frame according to claim 1 wherein said arcuate frame includes counterweights below the pivoting axis thereof so as to tend to return the arcuate frame to an upright condition.

10. A frame according to claim 1 wherein an x-ray detector is provided substantially on one side of the acruate frame, and on the other side of the arcuate frame is provided a motor for driving the said detector around said track.

* * * * *

UNITED STATES PATENT AND TRADEMARK OFFICE
CERTIFICATE OF CORRECTION

| | |
|---|---|
| PATENT NO. | : 7,497,617 B2 |
| APPLICATION NO. | : 11/571541 |
| DATED | : March 3, 2009 |
| INVENTOR(S) | : Benjamin Kingsley Stuart Peecock |

It is certified that error appears in the above-identified patent and that said Letters Patent is hereby corrected as shown below:

Title Page

At Item (74), change "Herronn" to --Herron--.

Column 4

Line 13, change "21," to --21--.

Claim 10, line 2, change "acruate" to --arcuate--.

Signed and Sealed this

Sixteenth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,497,617 B2 Page 1 of 1
APPLICATION NO. : 11/571541
DATED : March 3, 2009
INVENTOR(S) : Benjamin Kingsley Stuart Peecock It is certified that error appears in the above-identified patent and that said Letters Patent is hereby corrected as shown below:

Title Page

At Item (74), change "Herronn" to --Herron--.

Column 4

Line 13, change "21," to --21--.

Claim 10, line 63, change "acruate" to --arcuate--.

This certificate supersedes the Certificate of Correction issued June 16, 2009.

Signed and Sealed this

Fourteenth Day of July, 2009

JOHN DOLL
*Acting Director of the United States Patent and Trademark Office*